United States Patent
Izadpanah et al.

(10) Patent No.: US 11,380,434 B2
(45) Date of Patent: Jul. 5, 2022

(54) TELEHEALTH PLATFORM

(71) Applicants: Allen Izadpanah, Gaithersburg, MD (US); Jon Louthian, Clarksburg, MD (US); Donald Buck, Cockeysville, MD (US); Julian Werfel, Kensington, MD (US); Robert Graves, Fairfax Station, VA (US)

(72) Inventors: Allen Izadpanah, Gaithersburg, MD (US); Jon Louthian, Clarksburg, MD (US); Donald Buck, Cockeysville, MD (US); Julian Werfel, Kensington, MD (US); Robert Graves, Fairfax Station, VA (US)

(73) Assignee: VISUAL TELECOMMUNICATION NETWORK, McLean, VA (US)

( * ) Notice: Subject to any disclaimer, the term of this patent is extended or adjusted under 35 U.S.C. 154(b) by 193 days.

(21) Appl. No.: 16/221,536

(22) Filed: Dec. 16, 2018

(65) Prior Publication Data
US 2020/0194112 A1 Jun. 18, 2020

(51) Int. Cl.
*G16H 40/20* (2018.01)
*G06F 8/38* (2018.01)
*G06F 8/33* (2018.01)

(52) U.S. Cl.
CPC .............. *G16H 40/20* (2018.01); *G06F 8/33* (2013.01); *G06F 8/38* (2013.01)

(58) Field of Classification Search
CPC .............. G16H 40/20; G06F 8/38; G06F 8/33
See application file for complete search history.

(56) References Cited

U.S. PATENT DOCUMENTS

| | | | | |
|---|---|---|---|---|
| 2002/0055917 A1* | 5/2002 | Muraca | ................. | G16H 40/20 |
| 2002/0087355 A1* | 7/2002 | Rowlandson | .......... | G16H 50/30 705/2 |
| 2003/0216928 A1* | 11/2003 | Shour | ................... | G06F 16/958 705/2 |
| 2005/0203777 A1* | 9/2005 | Rosenfeld | ............. | G06Q 30/04 705/3 |
| 2013/0110537 A1* | 5/2013 | Smith | ................... | G16H 10/60 705/2 |
| 2013/0116526 A1* | 5/2013 | Javitt | ................. | G01N 27/3274 705/2 |
| 2014/0074506 A1* | 3/2014 | Oliver | .................... | G06F 19/00 705/3 |

(Continued)

*Primary Examiner* — John P Go
(74) *Attorney, Agent, or Firm* — NovoTechIP International PLLC

(57) ABSTRACT

In various formats and various technologies across the health care systems/locations, there is a huge need to integrate and make it easier for the user to apply all these technologies across the board, without the need to become an IT/software expert or hire one in-house, which is very expensive and duplicative effort for other similar organizations in the health care industry to do the same exact function. This document describes a software system that allows our system (ViTelNet) to design, configure, deploy, and run sophisticated custom applications across a variety of hardware platforms, without writing any code. In one example, we describe a method/system for the telehealth platform. In one example, we describe the development tools for such a platform. Many variations and examples are also presented.

17 Claims, 12 Drawing Sheets

(56) References Cited

U.S. PATENT DOCUMENTS

| | | | |
|---|---|---|---|
| 2014/0081659 A1* | 3/2014 | Nawana | A61B 5/1118 705/3 |
| 2014/0181741 A1* | 6/2014 | Apacible | G06Q 10/109 715/810 |
| 2014/0259094 A1* | 9/2014 | Narayanaswamy | H04L 47/20 726/1 |
| 2014/0278475 A1* | 9/2014 | Tran | G16H 80/00 705/2 |
| 2015/0347499 A1* | 12/2015 | Keen | G06F 16/24 707/736 |
| 2015/0379225 A1* | 12/2015 | Plasse | G16H 80/00 705/2 |
| 2016/0135755 A1* | 5/2016 | Lu | A61B 5/7221 600/301 |

* cited by examiner

TELEHEALTH PLATFORM

BACKGROUND OF THE INVENTION

In the recent years, telehealth has become extremely important to increase efficiency, reduce cost, provide the expertise to remote locations, increase collaborations, increase knowledgebase, reduce error in diagnosis, improve the health care system for all, increase access and speed, double-check the accuracy and consistency, increase the security and privacy for patients, keep the old records safely, access the old records from other locations, apply new methods for efficiency, e.g., AI, transmit large files, e.g., images, tagged or supplemented with opinions from multiple experts/specialists, and increase the life expectancy and improve the well-being for all humans across the globe. This has a great/positive social and economical impact across the globe, particularly in the United States, to manage and optimize the health care and its cost very efficiently.

In one example/aspect of our system/method, ViTelNet's continuum of care offerings in the telehealth space contain many use cases where a Pan Tilt Zoom (PTZ)-enabled camera is essential to support a remote clinicians ability to successfully support a patient encounter. Video conferencing is now a commodity, and as such, ViTelNet's customers may already have substantial investment in a video platform. In some cases, a customer may be using multiple third-party video platforms with multiple camera models that must seamlessly work together within the ViTelNet vCareNet platform. One of the core value propositions of VitelNet's business model is to provide seamless integration between disparate video platforms. Far End Camera Control (FECC), which is the ability to control a PTZ camera from a remote location, is accomplished differently in each video vendor's solution. ViTelNet's challenge is to provide the same FECC experience to clinicians within platform applications, regardless of the underlying video conferencing technology being used.

Thus, in various formats and various technologies, there is a huge need to integrate and make it easier for the user to apply all these technologies across the board, without the need to become an IT/software expert or hire one in-house, which is very expensive and duplicative effort for other similar organizations in the health care industry to do the same exact function. So, that would reduce the cost and increase efficiency. It would also improve the use across various domains, for example, for the formatting of images and privacy/security levels for the patient's data, between hospitals and various doctors. That results in less error, delay, cost, misdiagnosis, and loss of data.

However, the invention and embodiments described/addressed here, below, have not been addressed or presented in any prior art.

SUMMARY OF THE INVENTION

In one embodiment, we describe a method/system which overcomes the problems mentioned above, to reduce cost and increase efficiency.

For example, in one embodiment, the solution is to move FECC out of the third-party vendor's video platform into the ViTelNet vCareNet platform. This would require:

vCareNet native applications (applications that are targeted to a specific operating system, such as Microsoft Windows, Mac OS, or Linux) be given the capability to issue PTZ commands to either a Universal Serial Bus (USB) attached camera or a network attached CODEC controlled camera.

vCareNet native applications be given the ability to send camera PTZ commands to the vCareNet platform and receive PTZ commands from the vCareNet platform. The technology used to accomplish this is a web socket. More specifically, the web socket implementation provided by Microsoft Signal®. PTZ commands can be either basic or advanced. Basic PTZ commands instruct the camera to:

Incrementally move in a specified direction (up, down, left, or right).

Zoom in or out.

Position to a memorized preset, which specifies both direction and zoom.

Advanced PTZ command instruct the camera to:

Center the camera based on a user clicking or tapping a position on vCareNet application video window.

Drawing a box in the vCareNet application video window which results in basic PTZ commands being issued to the camera, until the boxed video area occupies the full video window.

Track a user's face to keep it centered in the video window.

To implement advanced PTZ commands, the current thinking is to have the vCareNet platform join each video conference as a participant, which gives the platform the ability to see the video conference. When the platform receives an advanced PTZ command from a vCareNet application, it uses a machine vision approach to issue the basic PTZ commands to the camera, until the view requested in the advanced PTZ command is achieved.

Other embodiments and solutions to increase efficiency and convenience are described below, in details.

DETAILED DESCRIPTION OF THE PREFERRED EMBODIMENTS

Figure 1:
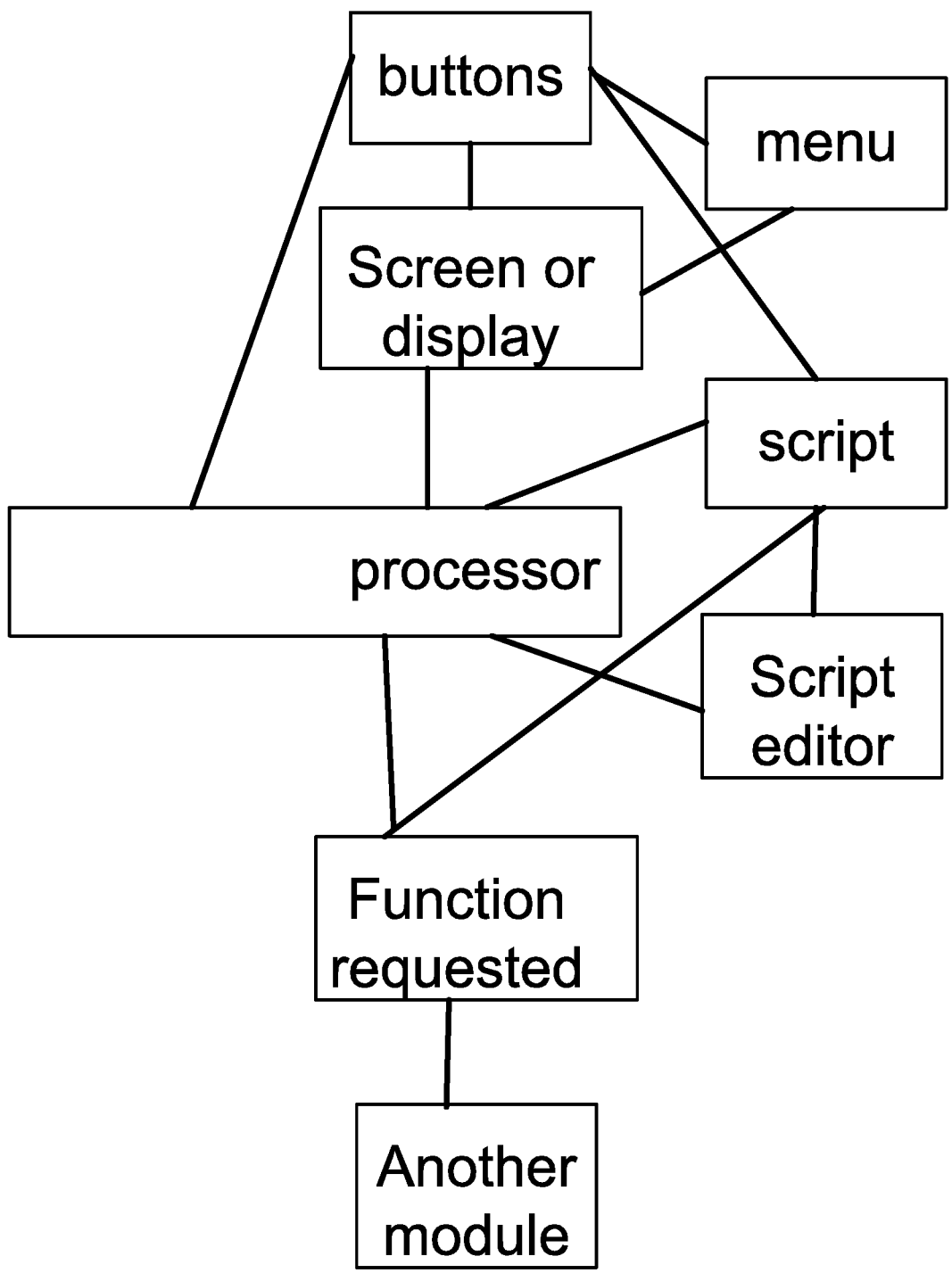
FIG. 1 is for one embodiment, as an example, for a system for scripting.

Here, we present various embodiments and examples in more details:

For example, for automated video switch for peripheral device integration, we have the following:

The typical situation/problem is that a customer wants to connect the video from a medical device to a telemedicine call. The call is occurring between a doctor on a tablet and a patient on a codec (in this case, e.g., a Cisco SX10). The codec can automatically switch from its primary camera to a plugged-in video source, when it detects a signal from the video source. No user interaction is required.

The medical device has 2 outputs: analog composite video and digital webcam over USB. The codec has 2 inputs: analog VGA and digital HDMI.

There are many devices on the market that will convert composite to VGA or HDMI. However, all the ones we could find would always output a signal to VGA or HDMI, even if there was no input RCA signal. The signal would be a video stream that says "no signal" or the like.

Because the devices would output a signal saying "no signal", the codec will not automatically switch back to the primary camera, when the medical device is turned off.

Our solution is the following: A USB webcam to HDMI adapter built from a Raspberry Pi. No custom hardware is required for this adapter, just a stock Raspberry Pi. However, the Raspbian OS (a flavor of Linux designed for the Raspberry Pi) has been customized to solve the problem. When the adapter boots, the HDMI port is turned off. When any webcam is connected to the adapter, it automatically starts playing the video and turns on the HDMI port. When the webcam is disconnected, the HDMI port is turned off, and the video player is stopped. The codec can now determine when to automatically switch to display the medical device video, and when to automatically switch back to the primary camera. Connection and disconnection can occur by physically plugging in or unplugging the USB to the medical device, while it is on, or by turning on and off the medical device, while it is plugged in.

We did not find any devices that would accept webcam input and output HDMI video. All of the devices we found were designed for standard video inputs, such as composite, VGA, HDMI, DVI, etc. Webcams expect a computer to be connected and manage the camera.

Using the webcam input, instead of the composite, and outputting to HDMI has the additional benefit of providing an all-digital path. The video quality is significantly better than going digital to analog to digital.

Other embodiments and examples are described below (some related to development tools and platform): (Please see Appendix 1, FIGS. 1-6.)

This section describes a software system that allows ViTelNet to design, configure, deploy, and run sophisticated custom applications across a variety of hardware platforms without writing code. (Please see Appendix 1, FIG. 1.)

At the highest level, the solution consists of a system containing the following components:

Application Development Tools, which provide the ability for a user to create full-featured applications without the need to write code.

The primary output of the development tools is a Master Control File (MCF) for the application. This MCF is used extensively by the deployment tools, engines, and shared services.

Deployment Tools, which use the MCF to create customized engines and services for a particular application, and deploy the MCF and other resources into the engines or services.

A plurality of Engines, running on different operating systems. These engines use the MCF at runtime to perform tasks such as generating forms, pages, and data-bound controls, mapping platform-provided functions and scripts to user actions, etc. The engine then executes the configured application. Examples of engine implementations include a Web engine, a WPF engine, an iOS engine, or an Android engine.

Client-agnostic Shared Services accessible through a services API, configured by and utilizing the MCF.

The following describes the high-level flow of events in creating, deploying, and executing an application in the system. The components and processes will also be described in further detail in subsequent sections.

Application development tools are used to create a master control file and other resources. The master control file consists of user-configured platform-agnostic abstract application, form, page, and control definitions, validators, background processes, and other application resources.

These resources are then deployed via the deployment tools to the appropriate engine(s) for the application.

The engine discovers and loads the functionality specified in the MCF from the deployed control and function libraries, configures the application, forms, pages, and controls, and executes the application.

At runtime, applications running on any of the plurality of engines make use of the same client-agnostic shared services. The services also take advantage of the master control file for configuration, customizing services, performing data validations, and other workflow.

Applicability of the Solution

The Development Tools, Deployment Tools, Runtime Engines and Shared Services are highly generic, and are not tied to a specific problem domain or "vertical market" (e.g., medical, legal, or finance). Knowledge about any particular vertical is encapsulated by functions, controls and other features, which are discovered at runtime by the tools, and are instantiated by the deployment tools, engines, and shared services dynamically in a generic manner.

For discussion purposes, this section will use examples from the medical field, but the tools and platform are not limited to this domain.

Application Development Tools

The Application Development Tools allow for the rapid creation of a wide range of highly sophisticated applications, by non-developers, without the need to write code. The tools are housed in a custom development environment that provides the ability to create and maintain applications via dragging, dropping, pointing and clicking. (Please see Appendix 1, FIG. 2.)

The tools produce a Master Control File (MCF), composed of abstract form, page, and control definitions, validators, application settings, and other metadata. These definitions contain all the information needed to define and run an application, but do not depend on any particular runtime platform. New platforms may be added at any time by developers, and the definition files will not need to be changed.

The tools depend on a plug-in architecture to expose functions, features, controls, and other assets to the user. Developers can add new functions, features, controls and assets to the system by implementing a set of required interfaces and copying the new assemblies into the tools' deployment location. The tools will automatically discover the new functionality and make it available to the tools user, giving them the ability to incorporate the new functionality into applications without writing code. This makes it very versatile and useful across the board for many functions/uses.

Application definition tasks that the user will perform include, but are not limited to, the following:

Create a new application definition.

Set properties at the application level. Examples of application level settings in the medical vertical include, but are not limited to:
  a. Configure the medical specialties fulfilled by the application.
  b. Configure that visibility and required status of fields on common dialogs. For example, patient search, patient creation, encounter creation, and others.
  c. Define how form data for each medical specialty is mapped to standard HL7 messages and sent out to EHRs when encounter lifecycle events occur.
  d. Define how form data for each medical specialty is mapped to standard CDA documents and sent out to interested parties when encounter lifecycle events occur.
  e. Define how standard DICOM fields are mapped into the custom fields in the application.
  f. Specify the background processes that should run for a given application.

Create and customize forms and pages. Customization options for forms in the medical vertical include, but are not limited to:
  a. Assigning the form to a specific medical specialty.
  b. Setting the initial status for a medical encounter backed by the form.
  c. Setting rules for which roles can create, advance, or close the form.
  d. Specify whether or not a password is required to close an underlying encounter.
  e. Identify which priorities are available for the underlying encounter.

Add controls to the forms. "Controls" can be anything from simple data-bound controls (such as text boxes or radio buttons) to complex fully featured components. Examples of full-featured controls in the medical field would include:
a. A National Institute of Health Stroke Scale control
  b. A video conferencing control that's automatically linked to a medical encounter
  c. A fully featured, user-aware worklist
  d. A DICOM import control
  e. An ICD10 code search and assignment control
  f. A real-time vitals control integrated with an external medical device Configure the controls on each form. Most controls have a wide variety of configuration options that can change their look, feel and behavior in many ways. All of these functionalities and behaviors are available to the platform user without writing any code.

Create workflow and navigate between forms.

Enhance the workflow by attaching function calls from the extensive built-in library, or by using scripts. Both scripts and functions can be configured to execute during a wide variety of user actions or application lifecycle events, including but not limited to:
  a. Clicking a button
  b. Changing the value in a text box, drop down, radio button list, check box list, or similar control.
  c. The starting or closing of the application.
  d. The loading, unloading, displaying, or hiding of a form page.
  e. The loading, unloading, displaying, or hiding of a specific control on a form.

Add state-and-data-aware validators for form data. Available validators in the system include, but are not limited to:
  a. Required field validator
  b. Cross-field conditionally required validators. If one field has a particular value, it can trigger another field to be required, as well.
  c. Cross-field conditionally disallowed validators. If one field has a particular value, it can trigger another field to disallow a value.
  d. Numeric validator, including verifying valid input, verifying allowed ranges of values, and other numeric validation tasks.
  e. Date validator, including verifying valid input, not allowing past or future dates, and other date validation tasks.
  f. Validators for more complex controls, such as an NIHSS stroke evaluation scale validator.

Configure the state machine for an encounter, including:
  a. Invoking background processes or other actions when the state changes
  b. Automatically running validations appropriate for the state change.

Configure code tables (lookups) for the application, and assign those lookups to list items like dropdowns, checkbox or radio button arrays, or list boxes.

Create and update dynamic database tables and columns, including creating new tables or columns, changing whether they are nullable or not, and other common tasks. See the Database Implementation section for more details.

Assign background processes that run at specified times, or that are triggered by application events (encounter created, report requested, etc.).

Note: At any point during the creation of the application, the user can invoke the deployment tools from with the development environment, and run the application against their chosen engine. This allows for rapid cycling between designing and testing the application, for quick feedback/improvement.

Deployment Tools

The deployment tools take the output of the development tools (including the control file, schema updates, images, scripts, and other assets), overlay them on the engine, and packages everything up into the appropriate bundles as required by the target runtime platform.

The deployment tools are separated into common tools (pre-deployment) and platform specific tools. The common pre-deployment tools run first, regardless of platform. The platform-specific tools then complete the task of preparing the application to run on the particular platform.

Common pre-deployment tasks include, but are not limited to, the following: (Please see Appendix 1, FIG. 3.)
  a. Update the schema of the target database.
  b. Update the code tables in the target database.
  c. Automatically generate and compile domain objects mapped to the customer and application specific schema updates.
  d. Platform specific deployment tasks vary significantly by platform, but all share the following high-level characteristics
  e. Gather all resources generated by both the development and pre-deployment phases.
  f. Assemble them into a known directory structure.
  g. Overlay them onto an instance of the engine or services.

h. Bundle the entire package as required by the target platform.
i. Copy the bundle to the target platform. The target platform can be simulators or actual devices.
j. Optionally run the application or services to allow for testing.

Run-Time Engines

The system consists of a plurality of run-time engines that run on different operating systems. Examples of engines include a web engine, a WPF engine, a UWP engine, an iOS engine, or an Android engine. (Please see Appendix 1, FIG. 4.)

For each platform, the engine consists of a similar set of components:

A run-time Data Context to store application data and configuration information.
Navigation services that display forms and navigate between them, display pop-up windows, etc.
Loaders (application, form, page, control, etc.) that read the abstract definitions in the control file and instantiate implementations for the current runtime platform.
The set of functions and validators required by the application, and configured via properties in the MCF.
A script engine that can be used to further customize runtime behavior.

Shared Services

The system includes shared services that are utilized by all runtime engines to perform business logic, access data from local databases or external systems and services, run background process, and perform other tasks. The shared services utilize the MCF as well, so that the applications running on the engines and the services all agree on the forms, settings, rules, validations, and other configurations that make the application unique. (Please see Appendix 1, FIG. 5.)

In addition to the application-specific functionality as driven by the MCF, the Shared Services provide some standard services that apply across all applications. Examples of standard services include, but are not limited to:

Real-time change update notification across all clients. If a user updates data in their application, the change is propagated in real-time to other users viewing the same data.
Change tracking.
Data extraction options, such as exporting data to CSV files
Vertical-specific common functionality can also be included, such as automatic field-level HIPAA logging for the medical vertical.

The shared services expose a dynamic API. APIs can be called by the client through a generic RPC-like mechanism. The shared services use a discovery mechanism at runtime to locate API implementations on demand as clients ask for them. This keeps the shared services generic, and allows new APIs to be exposed to applications by adding additional implementations of the API interfaces without needing to add code directly to the shared services.

Database Implementation

The system uses a unique approach to data storage, to allow for easy extension of the schema through the tools. In addition to standard SQL tables, the system incorporates "dynamic tables". The "dynamic table" concept is managed internally by 3 SQL tables: (Please see Appendix 1, FIG. 6.)

DynamicTableMetadata—This table holds metadata about all the dynamic tables in the system, including:
a. the table name
b. foreign key relationships
c. cardinality
d. etc.

DynamicColumnMetadata—This table holds metadata about all the dynamic columns in the system, including:
a. the dynamic table to which it belongs
b. the column name
c. the data type. This can include standard SQL data types, or system defined data types such as CodedValue, ICD10Code, Patient, etc.
d. the maximum length of the data, if applicable
e. the nullability
f. etc.

DynamicTableData—This table holds the user-provided data for each of the dynamic tables. It contains:
a. The dynamic table name that the data is associated with
b. The values of foreign keys that link this data to other data in the system
c. A DynamicFields XML column. This contains an xml representation of all the unique data for the row. It is made up of name/value pairs, where the name is the column name as specified in the DynamicColumnMetadata table, and the value is the data value provided by the user.

This system has several unique benefits:

It is easily extensible via the tools. To add new tables or columns, you simply add new rows to the DynamicTableMetadata or DynamicColumnMetadata tables, and allow the deployment tools to regenerate the business objects based off of the updated schema.
Dynamic tables, since they contain significant metadata, are indistinguishable from standard SQL tables when viewed in the tools during field-to-database mapping activities.
Dynamic tables, since they contain all required metadata, can be automatically converted to a standard SQL table at any time, if necessary for optimization reasons.

In one embodiment, Appendix 2 FIG. 1 describes the vCareCommand Telehealth Platform, as how our system is configured and arranged, which relates the remote monitoring, remote consultation, health eKiosk, virtual visit, and $1^{st}$ responder to the following modules/platform cloud services:

Configurable workflow modules, interoperability services, real time video and secure IM, patient data aggregation, imaging integration access and viewing, scheduling and routing, reporting and analytics, and AI.

These are also connected to $3^{rd}$ party telehealth solutions, as well as:

Multi-PACS, Multi-PHR, and Multi-HER.

Figure 2:
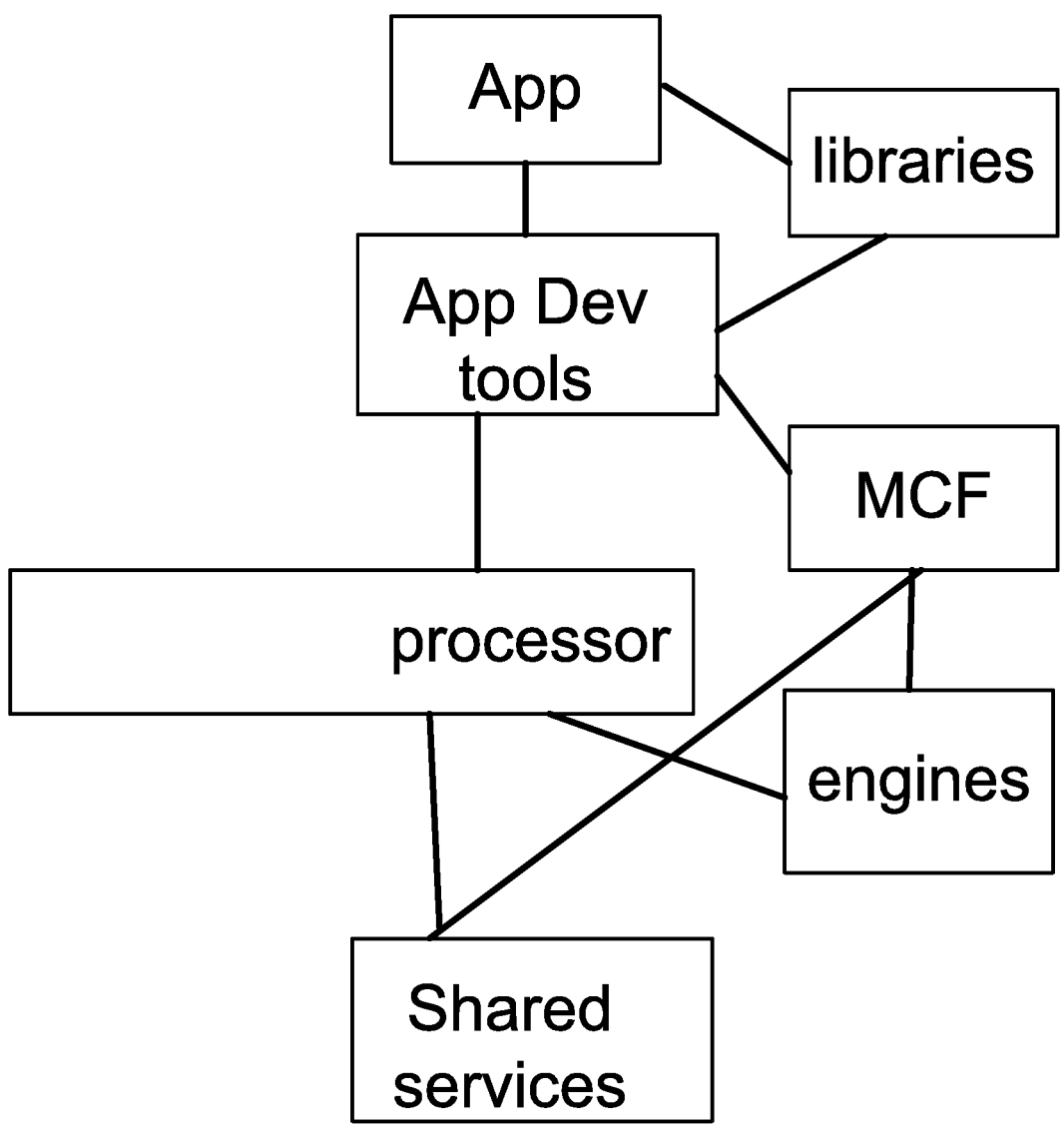
FIG. 2 is for one embodiment, as an example, for a system for application development tools.

In one embodiment, Appendix 2 FIG. 2 describes our enterprise platform advantages, regarding:

Data aggregation, configurable workflow, interoperability, and embedded imaging, with the details listed there.

Figure 3:
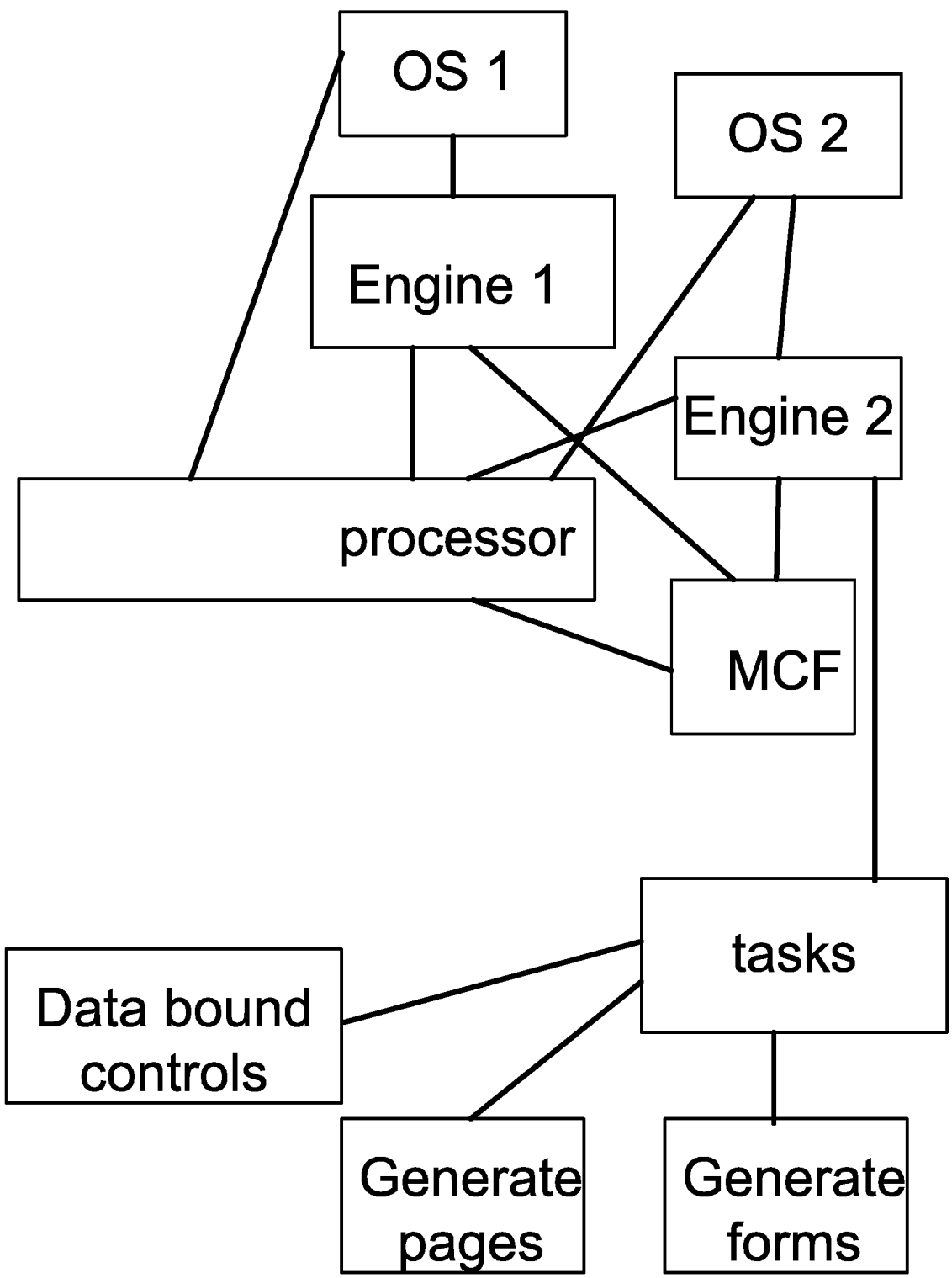
FIG. 3 is for one embodiment, as an example, for a system for MCF, engines, OS, and tasks.

In one embodiment, Appendix 2 FIG. 3/page 3 describes: vCareCommand, including customer enterprise, vCareNet software, and the cloud solution, with all the components listed there, as how they are connected and interact with each other.

In one embodiment, we have vCareCommand, related to consultation solution and customer solution. In one embodiment, we have vCareCommand with interoperable modular design, for integration with any health IT system, e.g., for:

Video and secure IM platform
Medical device integration
Clinical workflow and documentation
Scheduling and routing Integrated image recognition
PACS/RIS integration
Cloud based medical imaging
EMR/HER integration
Data aggregation In one embodiment, we have vCareNet for data and imaging, accessible by internal and partner providers. It can have EHR & HIE data, medical imaging, and home health data. For continuum of care, it can have specialist consultant, cloud imaging, home monitoring, and direct to consumer.

Figure 4:
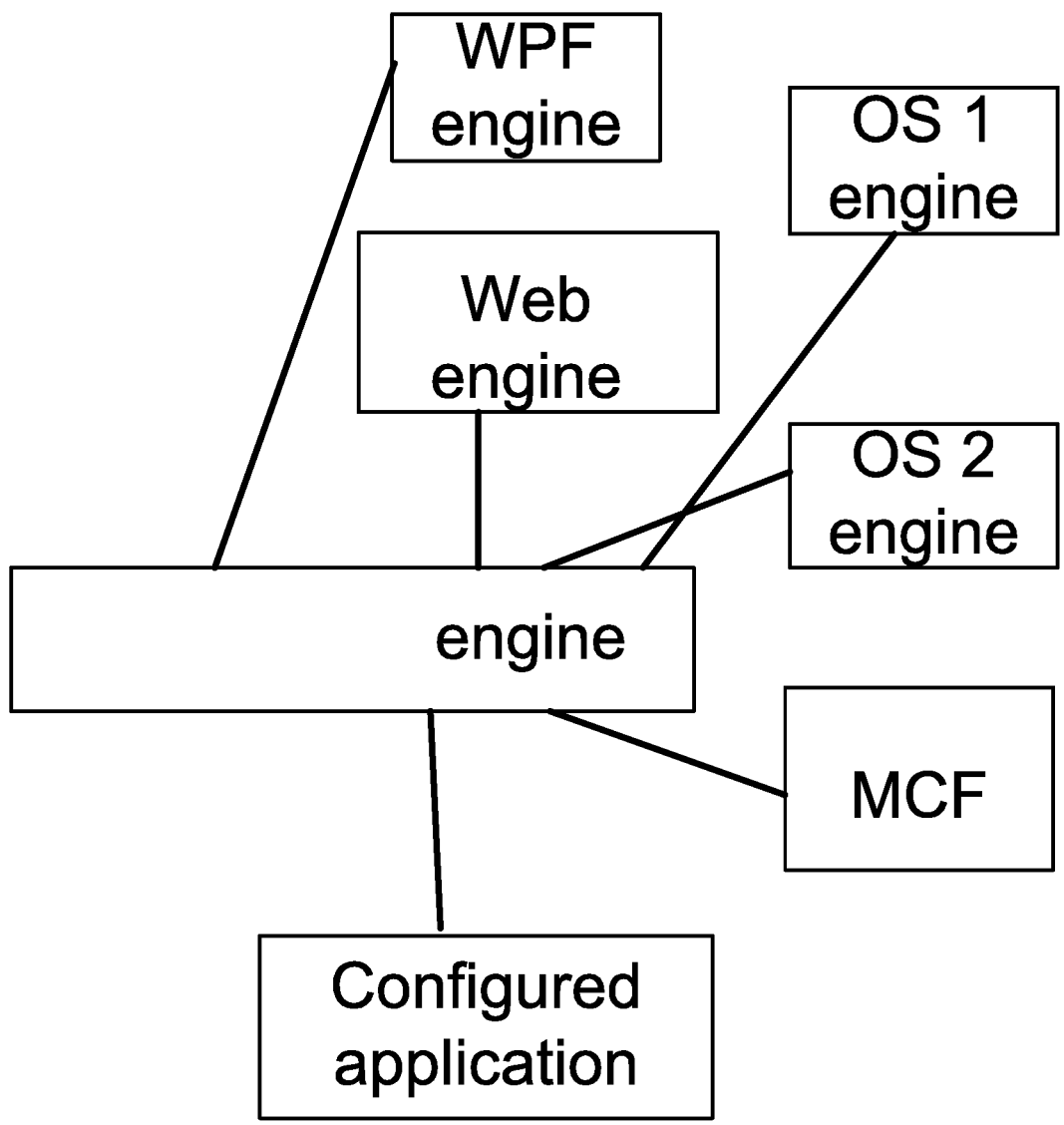
FIG. 4 is for one embodiment, as an example, for a system for engine.
Figure 5:
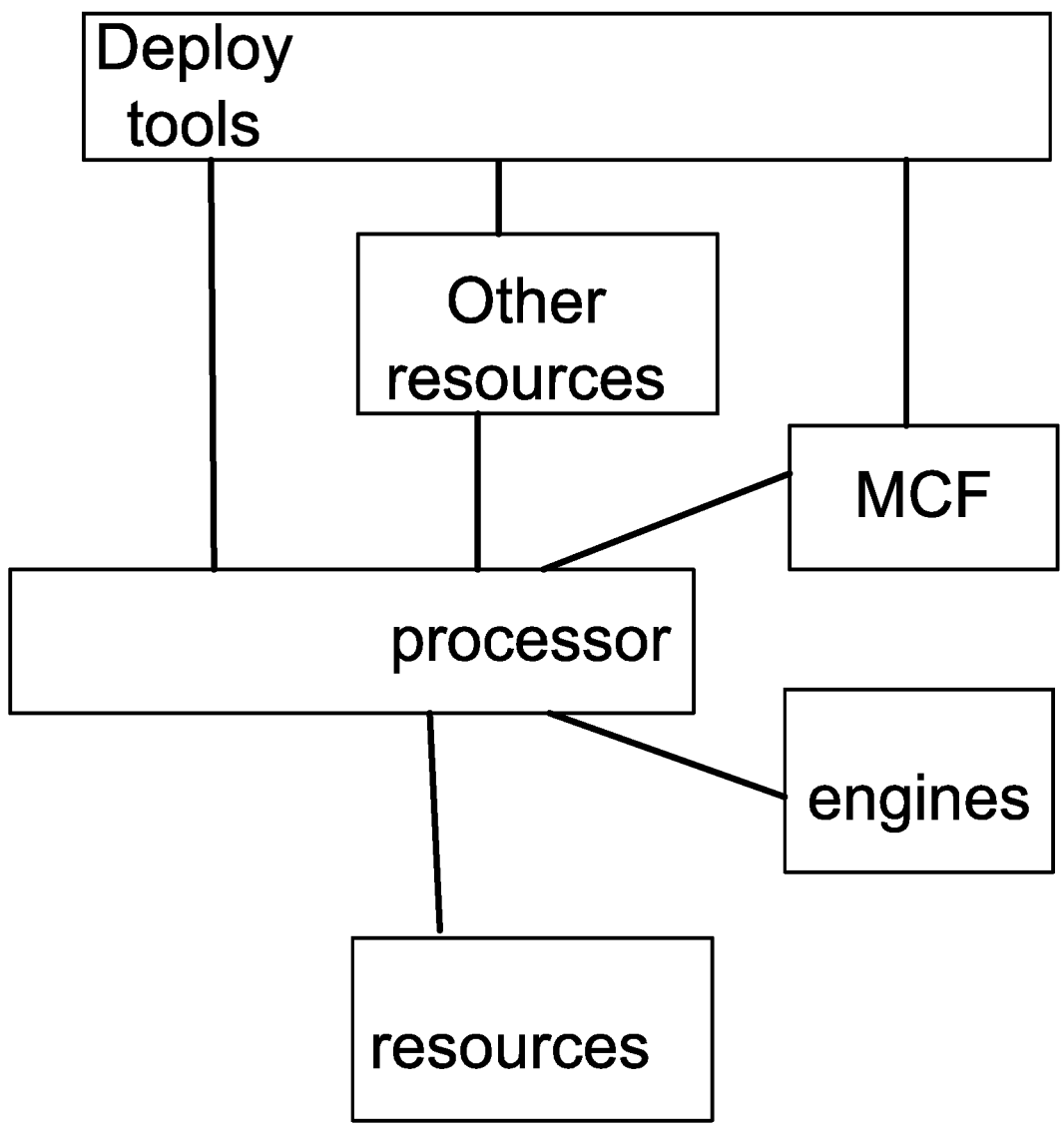
FIG. 5 is for one embodiment, as an example, for a system for MCF, engine, and deployment tools.

For clinician's workflow, it can have:
Uniquely configurable user experience
No coding is needed: fast and cost effective
Tailored on a per specialty basis
Eliminates barriers to clinician adoption FIG. 1 is for one embodiment, as an example, for a system for scripting. FIG. 2 is for one embodiment, as an example, for a system for application development tools. FIG. 3 is for one embodiment, as an example, for a system for MCF, engines, OS, and tasks. FIG. 4 is for one embodiment, as an example, for a system for engine. FIG. 5 is for one embodiment, as an example, for a system for MCF, engine, and deployment tools.

Figure 6:
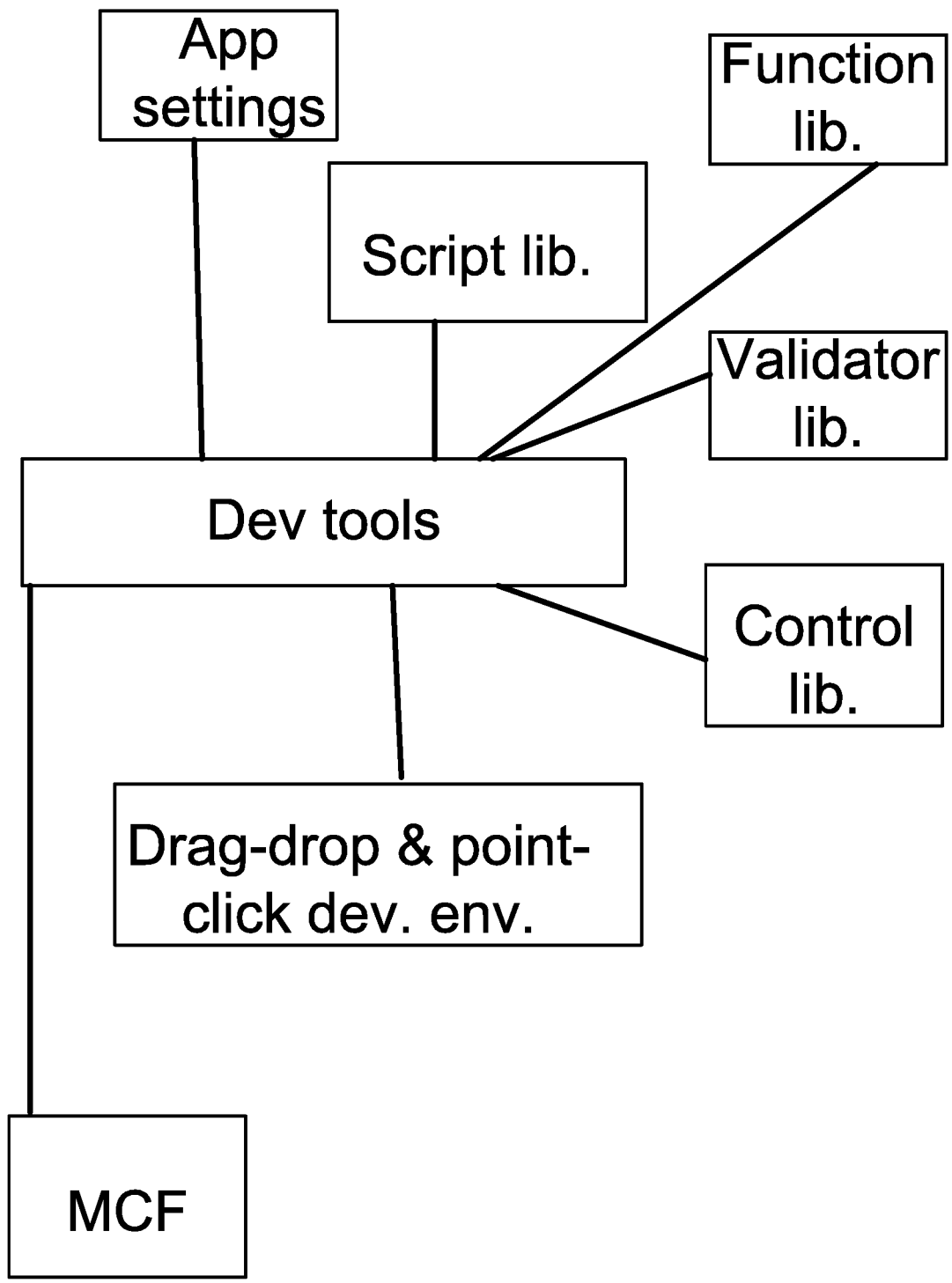
FIG. 6 is for one embodiment, as an example, for a system for MCF and Development Tools.
Figure 7:
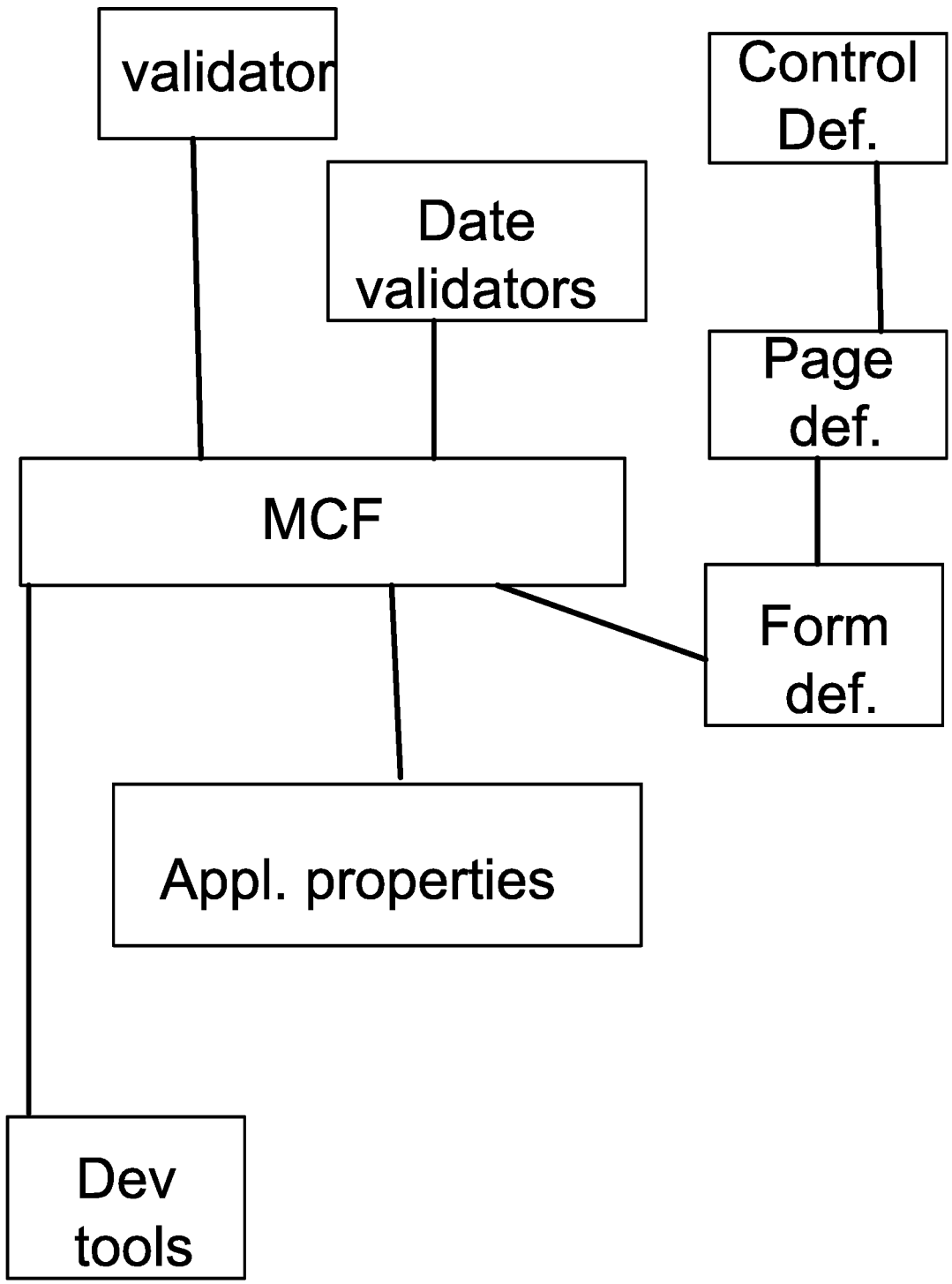
FIG. 7 is for one embodiment, as an example, for a system for MCF.
Figure 8:
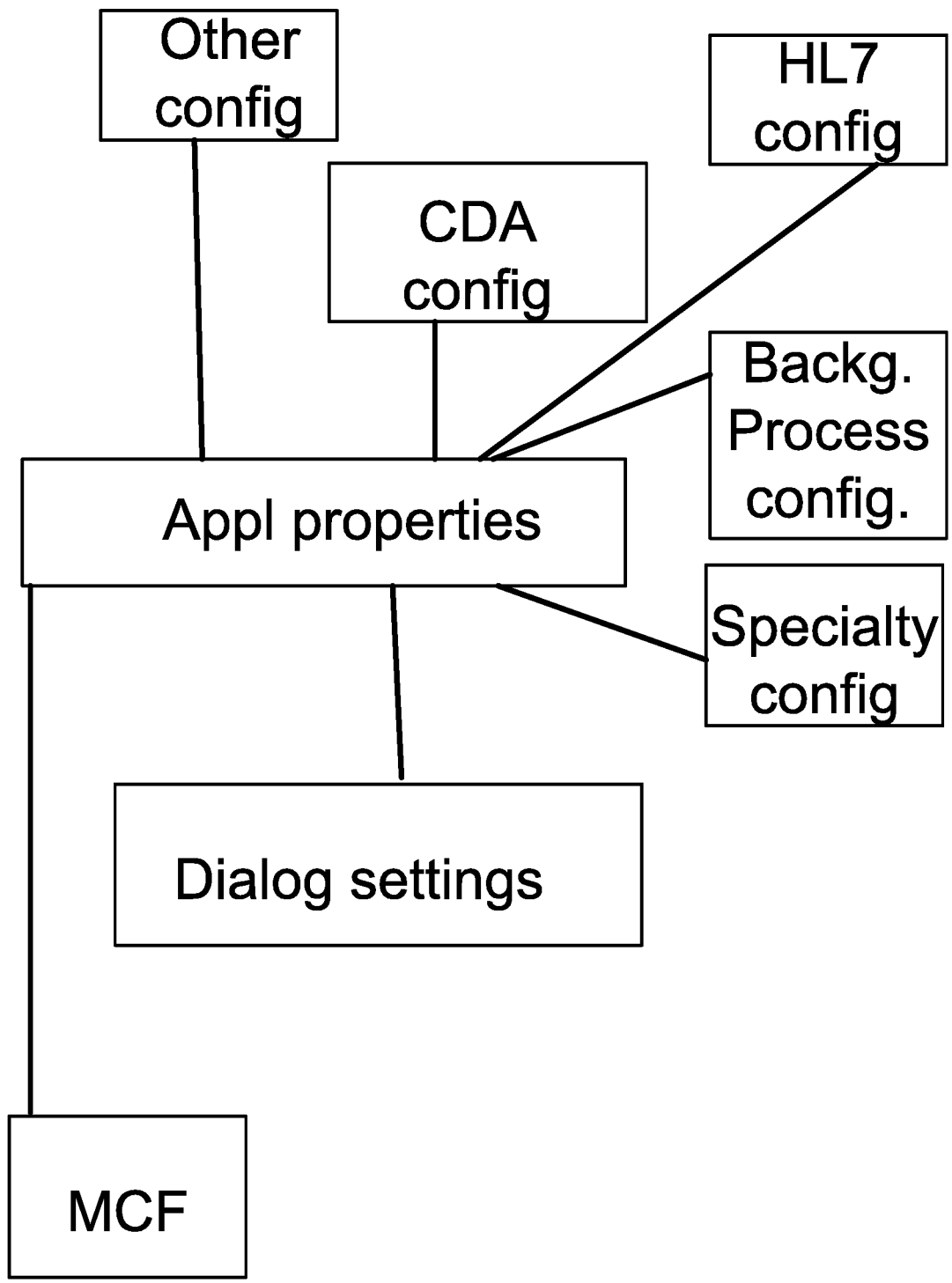
FIG. 8 is for one embodiment, as an example, for a system for application properties.
Figure 9:
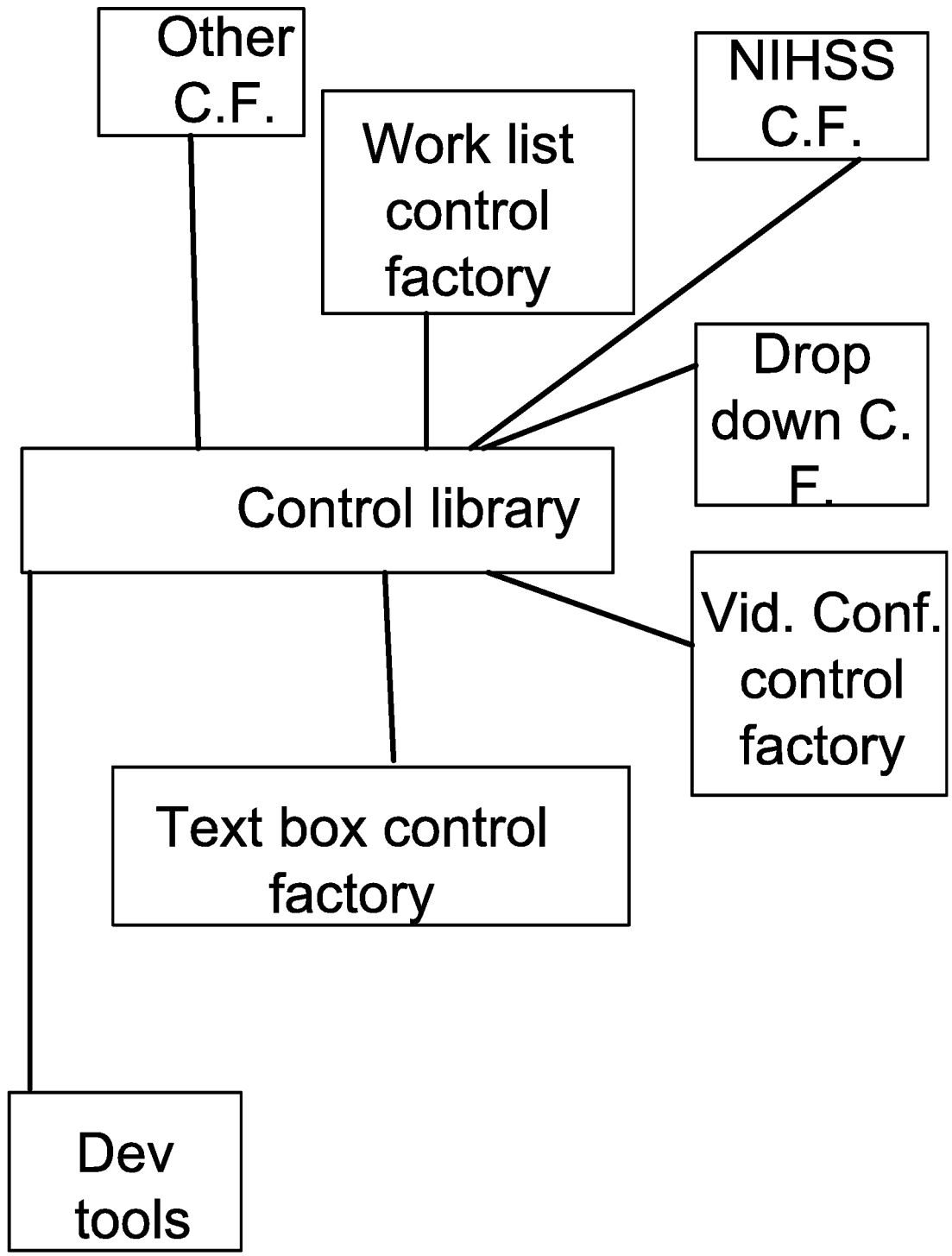
FIG. 9 is for one embodiment, as an example, for a system for control library.

FIG. 6 is for one embodiment, as an example, for a system for MCF and Development Tools. FIG. 7 is for one embodiment, as an example, for a system for MCF. FIG. 8 is for one embodiment, as an example, for a system for application properties. FIG. 9 is for one embodiment, as an example, for a system for control library.

Figure 10:
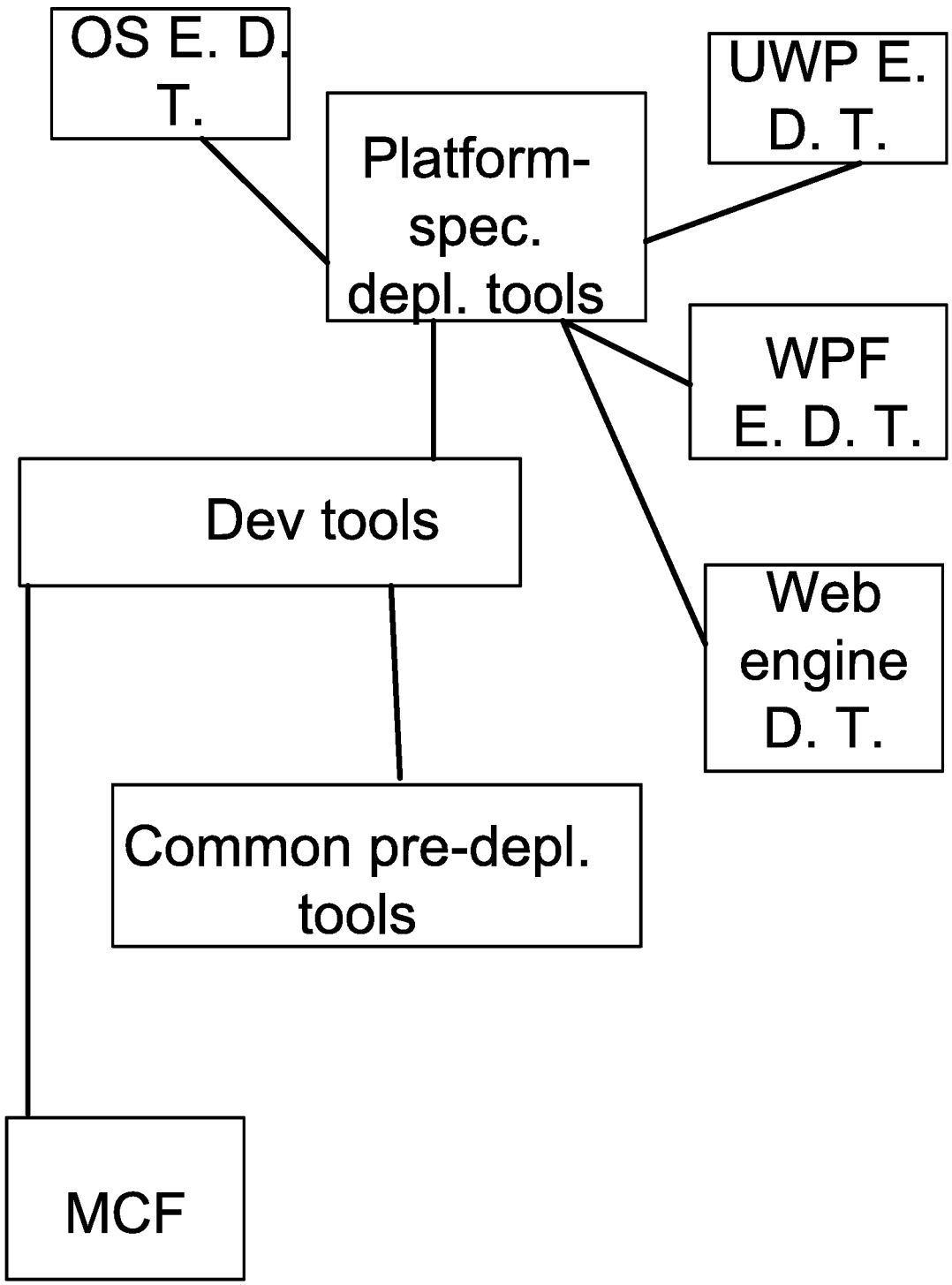
FIG. 10 is for one embodiment, as an example, for a system for development tools.
Figure 11:
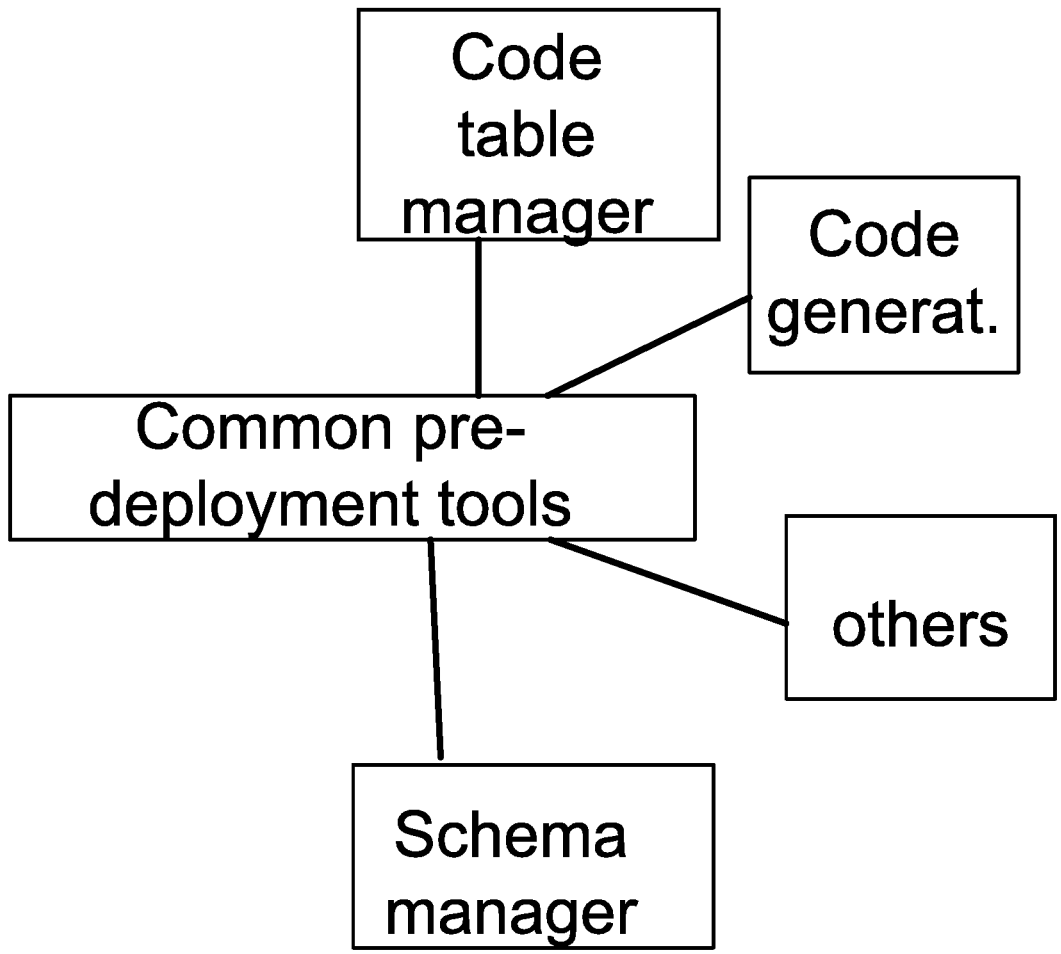
FIG. 11 is for one embodiment, as an example, for a system for common pre-deployment tools.
Figure 12:
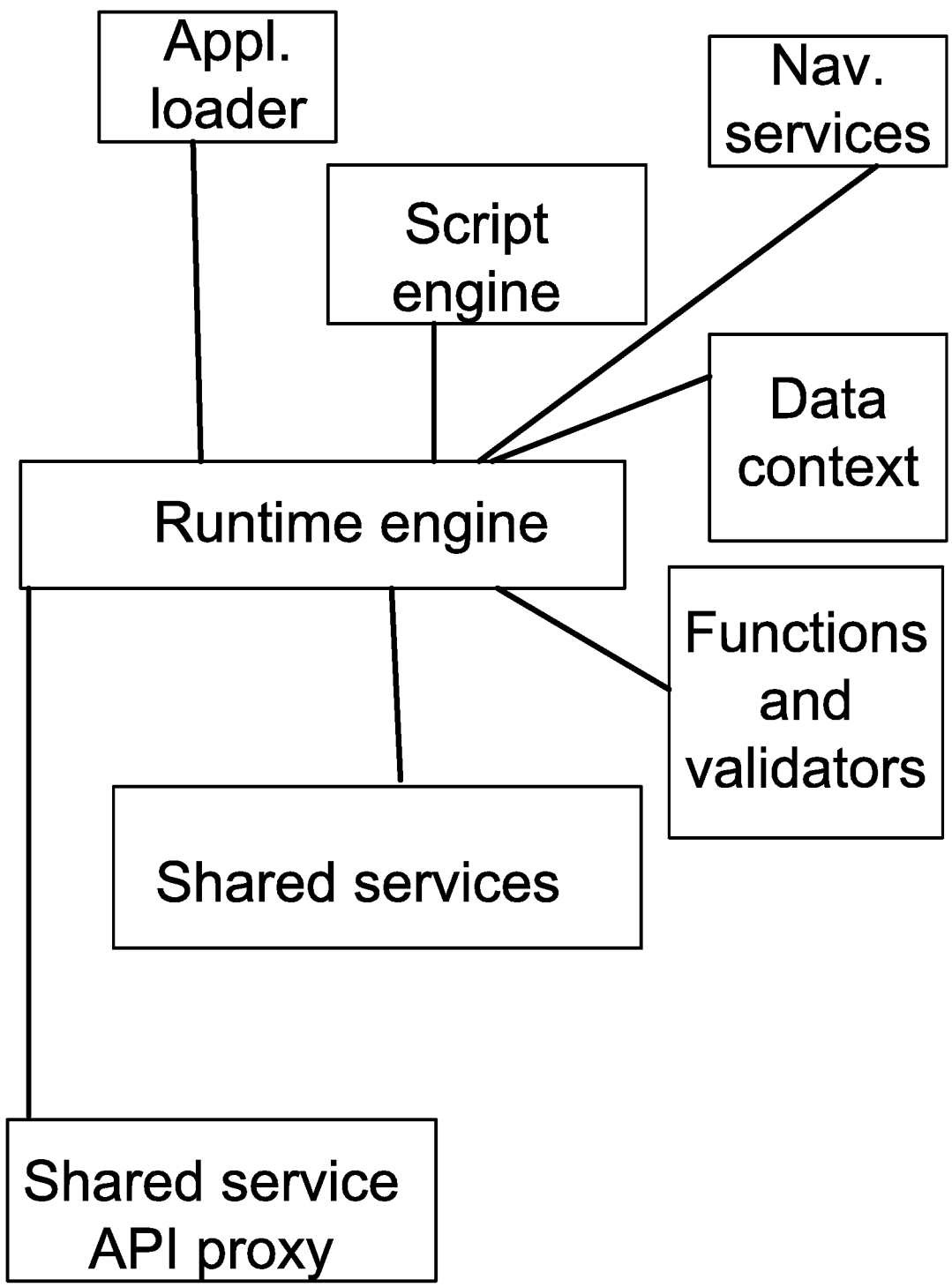
FIG. 12 is for one embodiment, as an example, for a system for run-time engine.

FIG. 10 is for one embodiment, as an example, for a system for development tools. FIG. 11 is for one embodiment, as an example, for a system for common pre-deployment tools. FIG. 12 is for one embodiment, as an example, for a system for run-time engine. Other details are shown in Appendices 1-2.

For integrated cloud imaging for telehealth, it can have: multi-format support and being ubiquitous (everywhere). For our cloud, any third party can be used (can hook in). We can have multi-vendor to choose from various solutions, as well as multi-service providers, multi-EHR (electronic health record), and multi-EMR (electronic medical record). So, the platform is very flexible and versatile, as it is not dependent on any specific solution or vendor, rather, anybody can hook in to it. Services for clinical purposes is on modular basis, where customers can choose from. The video conferencing can be chosen from various vendors, e.g., Zoom and WebEx. The camera and video conferencing can also be controlled independently and remotely.

For the messaging, with a $3^{rd}$ party, the care team can collaborate with and chat with other clinicians and experts. One important feature for singular run-time platform is interoperability, which is very unique feature, because others focus on specific care/solution, but ours is agnostic, and thus, can choose or aggregate all other solutions from various sources and vendors, to work together, for more efficiency and cost saving.

For image integration, we can use our own solution, with same viewer, e.g., for radiological, color, and EKG. Our solution makes it easier for the user for all services (such as single view), e.g., for lower configuration time (quick setup) and lower cost, as one platform for all vendors. One can setup or configure/customize from scratch with no coding/programming, using our tools and platform. Our libraries enable any new applications, by re-using features and scripts, which adapts to user's needs.

The user can add buttons from menus, with no coding, with specific function associated with it, for ease of use, immediately available. One can make a new function and window very fast in a few minutes, for user to apply or for user's interface/view. With block-chain or security modules, it can keep track of the owner or editor of each file, for privacy and security, as well as accountability and for being in compliance with the local laws, e.g., HIPAA (Health Insurance Portability and Accountability Act of 1996) in the United States.

Others can detect and diagnose or add to the current patient's file, as collaboration or second opinion. A chest X-ray can be released to a hospital, after the certificate or block-chain is verified, e.g., using PKI technology. It can be encrypted or encapsulated for security for the transmission of data. The diagnosis can come from humans/doctors or from AI assisted modules/sources.

For configurations, it can present dialogs, e.g., for specialties, to enable some properties, functions, or properties. The buttons from menus can be generated just by drag-and-drop, with specific functions or later customized further with more functions using our platform. Our engine in run time can build all functionalities.

Our work list form is an optional feature. We can have notes on videos for video conferencing. One can modify and configure to add to the code tables. The monitor/screen can have work-list and submit buttons/functions, displaying for areas such as main problems, referring physician, specialty, scale of the problem (with logic, calculating a score), notes or comments section (for drag-and-drop) (with codes built-in already) (e.g., for validation), video conf box (to drag in, for $3^{rd}$ party software), or the like, all built by/customized and placed on screen, using our platform, using no computer programming by the user, with ease of use/fast/flexibility, which is a huge advantage, that others cannot offer in this space. Also, see Appendices 1-2 for the examples and details.

The examples are also shown recently in the following videos: ViTelNet Overview video at https://youtube/hWaYEMxzX0g, and ViTelNet Executive Interview with Kathy Ireland Worldwide Business at https://youtu.be/LQy-PybIZvhU, and ViTelNet Development Platform Demonstration at https://youtu.be/aj1R5xjGyJ4. Also, see Appendices 1-2 for the examples and details.

Some of the embodiments shown in figures are: A system for telehealth platform, said system comprising: a user interface; a processor for processing and analyzing information received from a user through said user interface; a display; a script editor for writing and changing a script based on a computer language; a first script written based on said script editor; one or more buttons; a menu; wherein said menu is displayed on said display; said one or more buttons are chosen from said menu by said user; wherein said one or more buttons are displayed on said display; wherein said one or more buttons are associated with one or more functionalities; wherein said one or more buttons trigger said first script to run on said processor, when pushed or chosen on said display by said user; and wherein said first script produces said one or more functionalities through said processor on one or more other modules or on said system, with the following options:

a development tool set.
a web development tool set.
an operating system deployment tool set.
a web engine.
an operating system engine.
a shared services setup.

a master control file.
a dialog setting setup.
a background process configuration setup.
a form definition.
a page definition.
a control definition.
a validator.
a date validator.
an application setting.
a function library.
a control library.
a text box control factory.
a validator library.

The patient search can be done by admins/authorized people/doctors using passwords and biometrics. There can be a request for comments from a physician, to fill up a field, with a reminder, to enable another function. We can have a map for all the fields in use or on screen or available to us. One can write control modules for the screen and interface, for medical items or general-purpose items.

Some parts of the platform deal with library of functions, workflow engine (use graphic) (no coding is needed), and scripts (can do the changes remotely) (even for non-programmers). The scripts are very important feature here, to make it flexible and comprehensive for many applications and functions for various users.

The computer hardware/software can be centralized, distributed, or on cloud, such as server farms, or a laptop, or workstation for a doctor. The memory can be magnetic or optical, on tapes/discs, or a hard drive, RAM, ROM, or the like. The transmission can be wireless, WiFi, Bluetooth, cellular, by cable, wired, private network, Internet, or the like. These apply to all figures and embodiments mentioned in this disclosure.

Any variations/combinations of the above teachings for telemedicine/health and related areas are also intended to be covered by this patent application.

The invention claimed is:

1. A system for telehealth platform, said system comprising:
   one or more development tools configured to generate a master control file (MCF) using a plugin-based architecture;
   a plurality of deployment tools functionally coupled to the MCF, the plurality of deployment tools using the plugin-based architecture;
   a plurality of runtime engines functionally coupled to the MCF, the runtime engines using the plugin-based architecture, wherein each deployment tool of the plurality of deployment tools and a corresponding runtime engine of the plurality of runtime engines are configured for a specific platform; and
   one or more shared services functionally coupled to the MCF, the one or more shared services using the plugin-based architecture, wherein:
   the one or more shared services comprise:
      real-time change update notification across a plurality of clients;
      data extraction options; and
      vertical-specific common functionality;
   the MCF comprises component instructions including metadata including abstract form definition, page definition, control definitions, validators, and application settings;
   the plugin-based architecture is configured to create dynamic tables and columns to store custom data for each telehealth specialty;
   the plurality of deployment tools create workflow modules configured to run on the corresponding runtime engine and the shared services, the corresponding runtime engine and the shared services use the workflow modules combined with the instructions in the MCF to run a telehealth application;
   the plurality of runtime engines are configured to run the telehealth application on the specific platform for which it is configured based on the instructions in the MCF to perform tasks including generating forms and mapping platform provided functions and scripts to user actions; and
   the telehealth application is integrated with video hardware and software systems.

2. The system of claim 1, wherein the telehealth application is configured to implement an advanced cross-vendor far-end camera control system for Pan-Tilt-Zoom cameras.

3. The system of claim 1, wherein the validators comprise at least one of a stroke scale validator, a diagnosis validator, a multi-field conditional validator, required field checks, a conditional validator, a date range validator, and a numeric validator.

4. The system of claim 1, wherein the control definitions in the MCF comprise a configurable library of functions that can be attached to user interface elements and event triggers.

5. The system of claim 4, wherein the control definitions comprise at least one of encounter lists, appointment scheduling, query retrieve, a patient population management subsystem, text boxes, radio button groups, and diagnosis lists.

6. The system of claim 4, wherein the user interface elements comprise a configurable system for real-time chat among providers or between patients and providers, the configurable system being configured to allow video communication and transmission of images and documents.

7. The system of claim 4, wherein the user interface elements comprise a configurable system for synchronizing edits to a telehealth encounter among users viewing the encounter.

8. The system of claim 1, wherein the component instructions of the MCF comprise one or more actions that can be attached to system events including patient or provider alerts, background processing of results, and export of data to other systems.

9. The system of claim 8, wherein the component instructions of the MCF further comprise instructions to create messages and/or documents to be sent to other electronic health record systems on demand, or automatically at the conclusion of a telehealth encounter.

10. The system of claim 9, wherein the component instructions of the MCF further comprise instructions to configure an exchange of images with other systems.

11. The system of claim 1, wherein the component instructions comprise instructions to allow for provider, clinic, resource and appointment scheduling.

12. The system of claim 1, wherein the component instructions comprise instructions to define at least one of medical specialties, a lifecycle for each specialty encounter, common dialogs, custom roles and permissions specific to the telehealth application, and mapped permissions to functionality.

13. The system of claim 2, wherein the telehealth application is configured to extract raw data from an encounter into a portable format for analysis or import into other systems.

14. The system of claim 1, wherein the vertical-specific common functionality comprises automatic field-level HIPAA logging.

15. The system of claim 8, wherein the component instructions of the MCF further comprise instructions to allow for provider, clinic, resource and appointment scheduling.

16. The system of claim 15, wherein the component instructions of the MCF further comprise instructions to define at least one of medical specialties, a lifecycle for each specialty encounter, common dialogs, custom roles and permissions specific to the telehealth application, and mapped permissions to functionality.

17. The system of claim 1 wherein the MCF component instructions further comprise user roles, access controls, background processes, and lifecycle states of controls.

* * * * *